United States Patent [19]

Okamoto et al.

[11] Patent Number: 5,334,442
[45] Date of Patent: Aug. 2, 1994

[54] ORTHOPEDIC SHEET-LIKE COMPOSITION

[75] Inventors: Shigetomi Okamoto, Kyutaro; Masahiko Miwa, Uji; Takayuki Sekine, Urawa; Hiroshi Yamaguchi, Tokyo, all of Japan

[73] Assignee: Alcare Co., Ltd., Tokyo, Japan

[21] Appl. No.: 981,181

[22] Filed: Nov. 25, 1992

[30] Foreign Application Priority Data

Nov. 28, 1991 [JP] Japan ............... 3-339747

[51] Int. Cl.$^5$ ............................... A61F 5/04
[52] U.S. Cl. .................. 428/246; 428/252; 428/253; 428/272; 428/286; 428/287; 428/290; 428/314.4
[58] Field of Search ............... 428/246, 252, 253, 254, 428/272, 284, 286, 287, 290, 314.4; 128/90

[56] References Cited

U.S. PATENT DOCUMENTS

| | | | |
|---|---|---|---|
| 4,376,438 | 3/1983 | Straube et al. | 128/90 |
| 4,433,680 | 2/1984 | Yoon | 128/90 |
| 4,498,467 | 2/1985 | Kirkpatrick et al. | 128/90 |
| 4,502,479 | 3/1985 | Garwood et al. | 128/90 |
| 4,572,171 | 2/1986 | Wegner et al. | 128/90 |
| 4,574,793 | 3/1986 | Lee et al. | 128/90 |
| 4,668,563 | 5/1987 | Buese et al. | 428/230 |
| 4,683,877 | 8/1987 | Ersfeld | 428/317.7 |
| 4,800,872 | 1/1989 | Buese et al. | 128/90 |
| 4,856,502 | 8/1989 | Ersfeld | 428/253 |
| 4,946,726 | 8/1990 | Sandvig et al. | 428/76 |
| 4,984,566 | 1/1991 | Sekine et al. | 128/90 |
| 5,160,485 | 11/1992 | Jaillet | 428/253 |

*Primary Examiner*—Jenna L. Davis
*Attorney, Agent, or Firm*—Haverstock, Garrett & Roberts

[57] ABSTRACT

Sheet-like compositions that can be used to form orthoses or orthopedic devices to conform to any shape of a body part. The sheet-like compositions include a pliant sheet impregnated with a viscous water-curable resin that hardens when exposed to water. Both sides of the pliant sheet are covered with individual composite fabric portions, each composite fabric being of a triple-layered structure comprising a front face, a back face and an interconnecting portion, each composite fabric having sufficient open knit or weave to allow the passage of air and moisture therethrough. In some embodiments, a closed-cell foam material may be interposed between one side of the pliant sheet and one of the composite fabric portions, and adhesive means may likewise be incorporated into the overall structure to prevent dislodgement of the pliant sheet, the fabric portions and the foam cell material.

11 Claims, 6 Drawing Sheets

ORTHOPEDIC SHEET-LIKE COMPOSITION

Applicants hereby claim foreign priority benefits under 35 USC § 119 of corresponding Japanese patent application Ser. No. (Hei) 3-339747, filed Nov. 28, 1991.

BACKGROUND OF THE INVENTION

1. Field Of The Invention

The present invention relates to sheet-like compositions that can be used to form a wide variety of various articles, orthoses or orthopedic devices, all of which articles are easily conformable to any shape of a body part or any portion thereof. The present articles are useful to cover a body part or any portion thereof for the treatment or protection thereof in the fields of orthopedic surgery, sports and sports-related injuries.

2. Description Of The Prior Art

In the field of orthopedic surgery, orthopedic devices or articles such as splints, collars for cervical vertebra, corsets and braces for joints are used to cover and support injured parts of the body. Such devices can be used in the treatment of fractures, distortions and deformities, and particularly for correcting and immobilizing the injured parts. Meanwhile in the field of sports, similarly formed devices are used to protect parts of the body against injuries from external impacts.

From a manufacturing viewpoint, these devices are roughly divided into two categories or groups. Splints constitute the first group and are mainly used for such injuries as those involving fractures or distortions of limbs. Splints, in width and length sufficient to cover the injured parts of the body, are applied against the injured body part and an elastic bandage is wrapped around the circumference of the particular splint for support thereof. Collars, corsets, braces for joints and protectors constitute the second group. That is, according to the shape of the injured body part, or the part of the body to be benefitted with the supporting or protecting article, formed materials are produced in combination with other members such as stretchable fabric materials, belts, hinges, fasteners such as Velcro type fasteners, and the like so that the resultant combination of materials can be easily applied to or removed from the injured body part.

The constituent materials of each of these orthopedic devices needs to be formed into a device conforming to the body part in question. There are a variety of known orthopedic device forming methods in the prior art including a method whereby a laminate made of sheets of semi-hard aluminum and foam material is bent by hand or with tools, such as with a pair of pliers, along and around the injured body part. In addition, devices are formed with cardboard, initially softened by wetting with water, which cardboard is applied to and formed around the injured body part for subsequent drying into a rigid device. Another method of forming orthopedic devices involves impregnating a material comprised of multiple-folded layers of textile tape with gypsum or a water-curable resin. The impregnated material is accommodated in a tube-like cotton knit or a laminate of such layers with foam material, and brought into contact with curing water and thereafter applied to the injured body part as the material is hardened. A further method disclosed in Japanese Unexamined Patent Application Publication No. Sho 83-203155 involves bringing an open-celled foam material impregnated with a highly viscous water-curable resin into contact with water, thereafter applying the moistened material to and around the body part and maintaining the material in contact with the body part as the resin cures. Still further, a method of forming orthopedic devices disclosed in Japanese Unexamined Patent Application Publication No. Sho 83-50074 involves applying a polymerizable material to a fabric which has previously been impregnated with a curing agent, coating the treated fabric with a cover, and curing the fabric and cover composition while shaped in conformity to a body part.

However, all of the materials utilized to form the above-identified devices have significant limitations and drawbacks. For example, orthopedic devices and articles formed with materials which include aluminum sheets or cardboard have the drawback that the finished devices fit poorly to the body part. Water-curable materials with impregnated resins, despite having improved body fit, have many drawbacks because the residual water from the curing process does not sufficiently evaporate, thus leading to such problems as long-lasting dampness, discomfort because of stiffness during use of the devices, the tendency to cause bacterial growth due to the generation of a favorable environment between the skin and the orthopedic device with appropriate temperature and humidity for promoting bacterial growth, and the tendency to cause an unpleasant odor and dermatitis. Furthermore, since curing agents in general and water-curable resins particularly generate heat when cured, a material comprised of such a resin when applied to the entire surface of a substrate, raises a risk of causing a burn on the skin in close contact with the curing device due to accumulation of such heat from the curing process.

SUMMARY OF THE INVENTION

The primary object of the present invention is to provide an orthopedic sheet-like composition for forming orthopedic devices used for the immobilization or protection of a body part or a portion thereof, and which conforms to the shape thereof. The present water-curable resin-based composition is particularly of value in the fields of orthopedic surgery and sports as the sheet-like composition is easy to work and form into orthopedic devices, it allows easy removal of the excess water from the composition after the resin curing process, and it forms devices that are comfortable when worn.

According to the present invention, the above-mentioned objectives are achieved by covering both sides of a pliant sheet with a fabric portion, each fabric portion comprising a triple-layer structure as will be hereinafter further explained. The pliant sheet is previously impregnated with a viscous water-curable resin that hardens when exposed to water. In addition, a closed-cell foam material may be interposed between one side of the pliant sheet and one of the triple-layered fabric portions.

It is advantageous that natural fibers, man-made fibers such as inorganic fibers, regenerated or recycled man-made fibers, semi-synthetic fibers or synthetic fibers, or a combination of natural and man-made fibers be used for the composite fabric portions, the fabric portions being preferably structured in a triple-layered manner comprised of a front face layer, a back face layer independent of the front face, and a connecting part linking the two faces.

It is particularly advantageous to form such a triple-layered fabric structure on a double raschel knitting machine. As an example of the materials that can constitute the triple-layered fabric, natural fibers can be used for the front face, relatively fine synthetic fibers for the back face, and synthetic fibers with relatively thick filament can be used for the connecting part linking the foregoing two faces. In addition, it is advantageous to adopt a circular-knit, triple-layered structure by use of tack fiber. Without limiting the triple-layered fabric to a knitted article, woven fabric can also be used. As for the connecting part, the size or number of the constituent threads should be such that the resulting density does not impair the water transport properties or air permeability of the final fabric structure.

According to the present invention, before application to the body part, the sheet-like composition is made into a one-piece article containing a pliant sheet impregnated with a water-curable resin which is sandwiched between a pair of double-faced sterically knitted triple-layered fabric portions. When the sheet-like composition is dipped in water, the water infiltrates through to the inside portion of the composition and reaches the curable pliant sheet through the interstitial voids between the fibers in the connecting part provided in the triple-layered fabric portions. After the water-containing sheet-like composition is applied to the desired body part and formed into an appropriate shape, the water, which has infiltrated through the fabric portions to the water-curable pliant sheet, reacts with the impregnated resin on the pliant sheet which cures and hardens the composition into a device with the desired shape. After the curing reaction is complete, residual water diffuses to the outside through the voids between the connecting fiber part in the composite fabric portions and such residual water is rapidly removed.

Where a foamed cell material is incorporated in the sheet-like composition, water which infiltrates the sheet-like composition does not infiltrate inside the closed-cell foam material because the cells are not interconnecting ones. Therefore, the buffering action inherent in the foam material is maintained even after the curing of the sheet.

Owing to its triple-layered structure, the composite fabric has a large number of voids inside it which provides beneficial water transport and air permeability. Therefore, water needed for the curing reaction is supplied in a sufficient amount to the impregnated resin on the internal pliant sheet and extra water is discharged outside through the fabric's connecting part without being trapped inside the fabric itself.

BRIEF DESCRIPTION OF THE DRAWINGS

FIG. 4b is a rear elevational view of the splint shown in FIG. 4a;

FIGS. 8a, 8b and 8c are each photographs of an example of one of the triple-layered fabric structures formed in accordance with the teachings of the present invention wherein FIG. 8a is a view of the front or top face of the fabric structure, FIG. 8b is a view of the back or bottom face of the fabric structure, and FIG. 8c is a side view thereof;

FIGS. 9a, 9b and 9c are each photographs of another example of one of the triple-layered fabric structures formed in accordance with the teachings of the present invention wherein FIG. 9a is a view of the front or top face of the fabric structure, FIG. 9b is a view of the back or bottom face of the fabric structure, and FIG. 9c is a side view thereof; and FIGS. 10a, 10b and 10c are each photographs of yet another example of a triple-layered fabric structure formed in accordance with the teachings of the present invention wherein FIG. 10a is a view of the front or top face of the fabric structure, FIG. 10b is a view of the back or bottom of the structure, and FIG. 10c is a side view thereof.

DESCRIPTION OF THE PREFERRED EMBODIMENTS

The present invention will be described in detail with reference to the attached drawings. Embodiments of the invention will now be explained by way of examples and with reference to the accompanying drawings.

Figure 1:
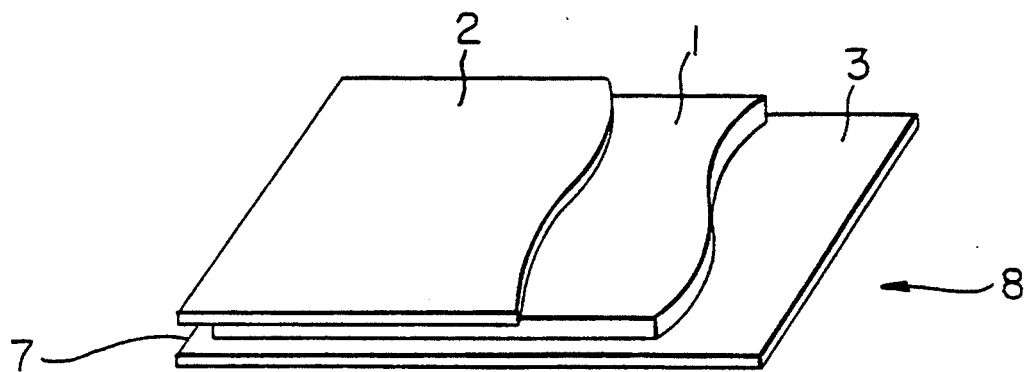
FIG. 1 is a partial cut-away perspective view of one embodiment of the present invention.

FIG. 1 is a partial cut-away perspective view of one embodiment of the present invention. Reference numeral 8 indicates an orthopedic sheet-like composition comprising a pliant sheet 1, particularly useful when formed in a rectangular shape, that is impregnated with a water-curable resin. On each respective side of pliant sheet 1, a composite fabric portion, as indicated by reference numerals 2 and 3, is placed in contact therewith, each fabric portion 2 and 3 having a somewhat larger area than that of pliant sheet 1. Thus pliant sheet 1 does not protrude from the periphery of fabric portions 2 and 3 as indicated at 7 in FIG. 1.

Figure 2:
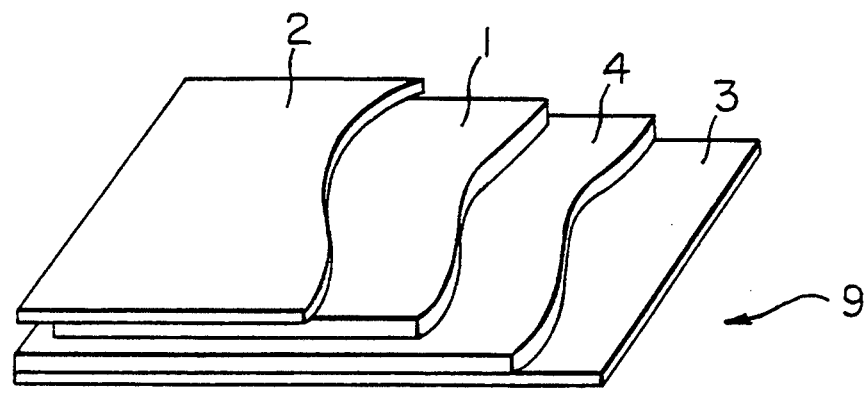
FIG. 2 is a partial cut-away perspective view of another embodiment of the present invention.

FIG. 2 is a partial cut-away perspective view of another embodiment of the present invention wherein the same reference numerals as used in FIG. 1 are utilized in FIG. 2 to refer to equivalent parts of the embodiment. As in FIG. 1, fabric portions 2 and 3 of composition 9 are respectively placed on opposite sides of pliant sheet 1 which is impregnated with water-curable resin and can be rectangular in shape. However, unlike the embodiment of FIG. 1, one of the composite fabric portions, namely fabric portion 3, does not directly contact pliant sheet 1, but instead, a closed-cell foam material 4 is interposed between pliant sheet 1 and fabric portion 3.

Figure 3:
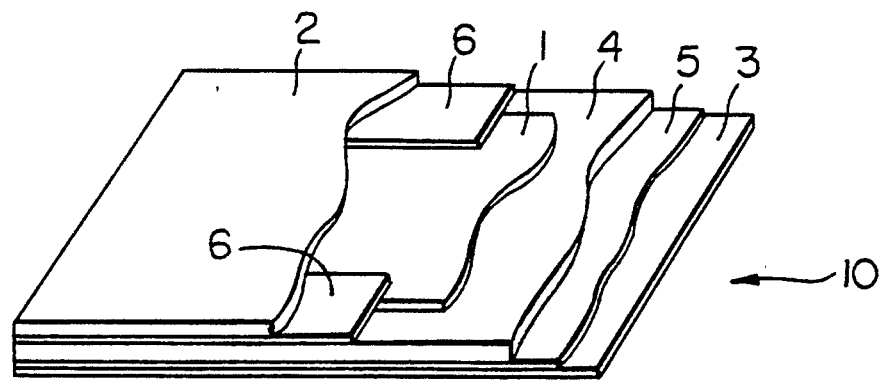
FIG. 3 is a partial cut-away perspective view of yet another embodiment of the present invention.

FIG. 3 is a partial cut-away perspective view of yet another embodiment of the present invention, composition 10, wherein the same reference numerals as in FIG. 2 are utilized to refer to equivalent parts. As in the constructions illustrated in FIGS. 1 and 2, on each respective opposite side of pliant sheet 1, which sheet is again impregnated with a water-curable resin, is placed a fabric portion, namely fabric portions 2 and 3, each fabric portion having a larger area than that of pliant sheet 1. Here again, one of the fabric portions, namely fabric portion 3, does not directly contact and overlap pliant sheet 1 as a closed-cell foam material 4 is again interposed between pliant sheet 1 and fabric portion 3. In this particular arrangement, however, fabric portion 3 and closed cell foam material 4 are linked together by way of adhesive means 5. Meanwhile, another adhesive means, such as a plurality of pressure sensitive double coated tape 6, is placed on the peripheral area between fabric portion 2 and pliant sheet 1. The foregoing adhesive means combination provides a means for securing and preventing the dislodgment of pliant sheet 1, fabrics 2 and 3, and closed-cell foam material 4.

In the above-mentioned examples, fabric portions 2 and 3 have an area larger than that of pliant sheet 1. It goes without saying, however, that fabric portions 2 and 3 may have an area equal to that of pliant sheet 1.

Possible materials for use as a pliant sheet include those various materials that have been employed in water-curable gypsum bandages for orthopedic surgery, including glass fiber, carbon fiber, polyester fiber, polyvinylidene chloride fiber, polypropylene fiber, acetate fiber, rayon and cotton. More particularly, the sheets described, for example, in Japanese Unexamined Patent Application Publication Nos. Sho 60-24285, Hei 2-71740, Sho 04-85659 and Sho 63-11165 as well as those described in Japanese Examined Patent Application Publication Nos. Hei 2-57940 and Hei 3-36543 are also usable.

Possible water-curable resins for impregnating a pliant sheet include those various materials which previously have been employed in forming water-curable bandages used for orthopedic surgery. These materials include compositions primarily comprised of polyurethane prepolymers synthesized from polyisocyanates such as diphenylmethane diisocyanate, tolylene diisocyanate, naphthylene diisocyanate, tolydiene diisocyanate, isophorone diisocyanate, and xylene diisocyanate. The resins can also be comprised of polyols such as polyester polyols, polyether polyols, polybutadiene polyols and acrylic polyols. In addition, the resins can include such polyurethane and polyol polymers mixed with catalysts, stabilizers and defoamers which are, for example, bis (2,6-dimethyl morpholino) diethyl ether, methane sulfonic acid and silicone. More particularly, the use of the resins described, for example, in Japanese Unexamined Patent Application Publication Nos. Sho 62-172008, Sho 60-48184, Sho 58-177655, Sho 58-175561 and Hei 2-26983 are likewise possible.

Possible closed-cell foam materials include those closed-cell foam materials, for example, made of polyethylene, polypropylene, polyvinyl chloride, polyurethane, neoprene rubber, polybutadiene, chlorinated polyethylene, natural rubber and silicone.

The present triple-layered fabric can be made on a double raschel machine which, owing to the presence of two parallel flat beds of knitting needles, allows the machine to compose a front face side and a back face side while simultaneously linking the two faces together thereby forming a knitted composite fabric. Alternatively, a circular-knit, triple-layered fabric can be made by means of a knitting machine equipped with two circular needle beds, such as where a dial-type and a cylindrical-type needle bed are disposed vertically to each other. Such a knitting machine forms a knitted fabric with a front face side and a back face side while simultaneously linking the two faces by way of tack tissue. Without limiting the sheet-like compositions of the present invention to knitted articles, composite woven fabrics can also be used in the present invention.

To be more specific, triple-layered fabrics are roughly divided into the following three types, any of which can be selected depending upon the purpose and application:

1. a double-face type in which both sides, front face and back face, are composed of flat tissue;
2. a reversible type in which either the front face or the back face is composed of mesh, while the other face is composed of flat tissue; and
3. a honeycomb type in which both sides, front face and back face, are composed of mesh.

The textile materials to be used in the composite fabric portions depend on the specific applications and purposes. Such textile materials include, but are not particularly limited to, natural fibers, man-made fibers such as inorganic fibers, regenerated man-made fibers, semi-synthetic fibers or synthetic fibers, or a combination of natural and man-made fibers. In particular, for the connecting part between the front and back face of the present fabric portion, a relatively rigid, thick monofilament or mono-multifilament fiber can be used. In addition, monofilament or mono-multifilament fiber of about 15 denier to about 220 denier is preferred in order to form and maintain a stable article shape.

The sheet-like composition according to the present invention comprising, at least in part, a pliant sheet 1 impregnated with a water-curable resin, and a pair of composite fabric portions 2 and 3 contacting at least one side and covering both sides of pliant sheet 1, is stored and sealed within a package filled with inert gas to prevent the infiltration of moisture from the outside. Just prior to the application of the sheet-like composition to the body part, the package is opened and the sheet-like composition is taken out of the package and dipped in a water bath. The composition is subsequently taken out of the water bath, lightly shaken to remove any extra water, applied to the predetermined part of the body and deformed by hand to conform to the shape of the body part. The whole sheet-like composition is wrapped with bandages and the like to fix the article in a final shape. As the composition is shaped around the body part, the water-curable resin which has contacted water reacts with the water, cures and starts hardening. After a lapse of time anticipated for such resins, the sheet-like composition completely hardens, forming an orthopedic device or article that provides an exact fit to the body part, or portion thereof.

Figure 4A:
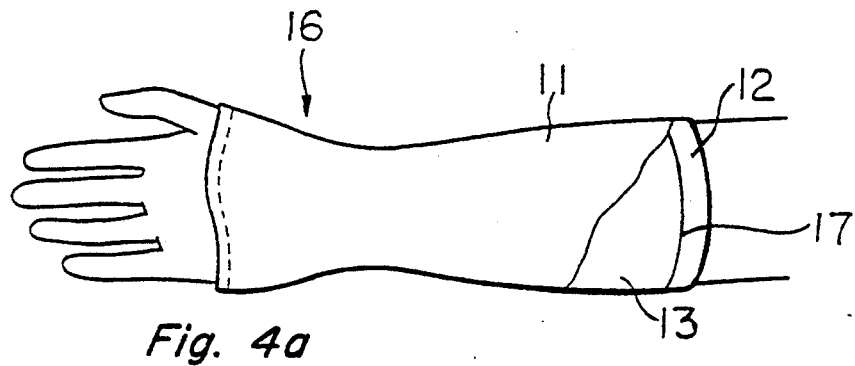
FIG. 4a is a front elevational view of a splint formed according to the teachings of the present invention, the splint being shown in partial cut-away and applied to a forearm.
Figure 4B:
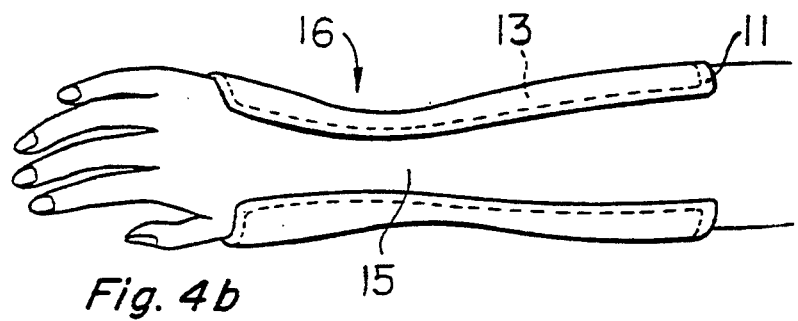

FIGS. 4a and 4b are front and rear views respectively of a splint 16 which is formed by use of the sheet-like composition of the present invention, the splint 16 being applied to a forearm 15 and being shown in partial cutaway for clarity purposes in FIG. 4a. A water-curable resin-containing sheet 13 interposed between fabric portions 11 and 12 is hardened into splint 16 in the shape of a forearm by the curing of the resin contained therein. Edge 17 of pliant sheet 13 is covered with fabric portions 11 and 12 and does not directly contact the skin. Edge portion 17 is likewise not touchable from the outside. Therefore, the wearer should have no apprehension of pain from skin contact with the hardened sheet.

Figure 5:
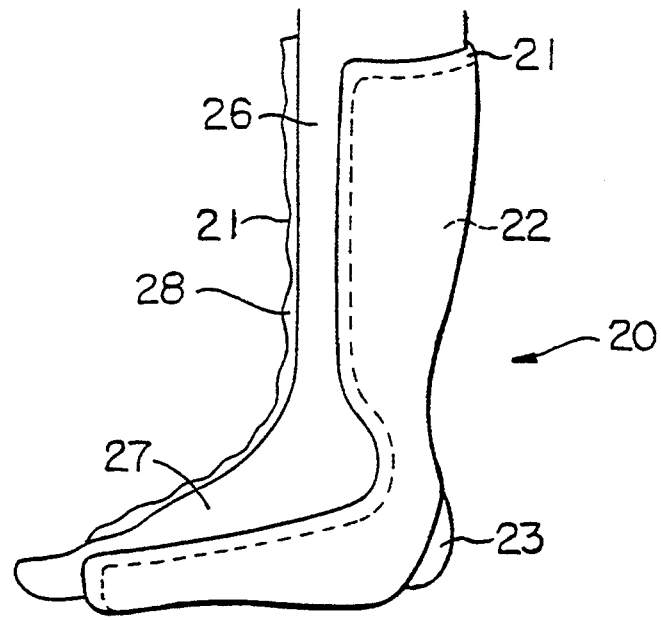
FIG. 5 is a side elevational view of a splint formed according to the teachings of the present invention, the splint being shown applied to a lower leg.

FIG. 5 is a side elevational view of a splint 20 which is likewise formed by use of the sheet-like composition of the present invention, the splint 20 being applied to a lower leg 26 and foot 27. Underlying hardened sheet 22 is located between exterior composite fabric 21 and interior composite fabric 28. At the splint portion corresponding to heel 23, the sheet-like composition including the fabric portions 21 and 28 and the hardened sheet 22 is cut-away as illustrated.

Figure 6:
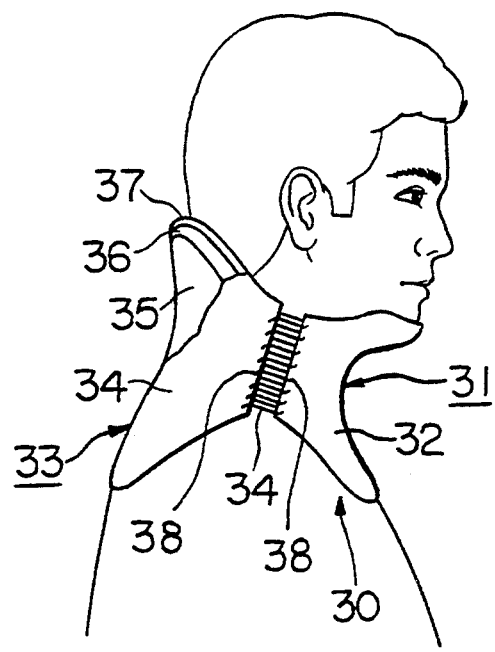
FIG. 6 is a side elevational view of a cervical vertebra type collar formed according to the teachings of the present invention, the collar being shown in partial cut-away and applied to the cervical area.

FIG. 6 is a side elevational view, along with a partial cut-away thereof, illustrating the applied state of a cervical vertebra collar 30 formed by use of the sheet-like composition of the present invention. Cervical collar 30 is comprised of a front support plate 31 having an exterior composite fabric 32, and a back support plate 33 having an exterior composite fabric 34, a hardened sheet 35, closed cell foam material 36 and an interior composite fabric 37. An embodiment of collar 30 for protection of cervical vertebra is prepared by the following steps: prepare and moisten two flexible closed-cell foam containing sheet-like compositions similar to the compositions shown in FIGS. 2 or 3; apply the moldable compositions to the front and back portions of a neck respectively; and form the two compositions respectively to the front and back portions of the neck. Once formed and cured, the front composition represents the front support plate 31 and the rear composition represents the back support plate 33. A plurality of holes 38 are thereafter bored into the vertical edge portions of each aligned opposite end portion of front support plate 31 and back support plate 33, the holes 38 being adapted for receiving a string 34 for attaching the two support plate portions at opposite sides thereof into completed collar 30.

Figure 7:
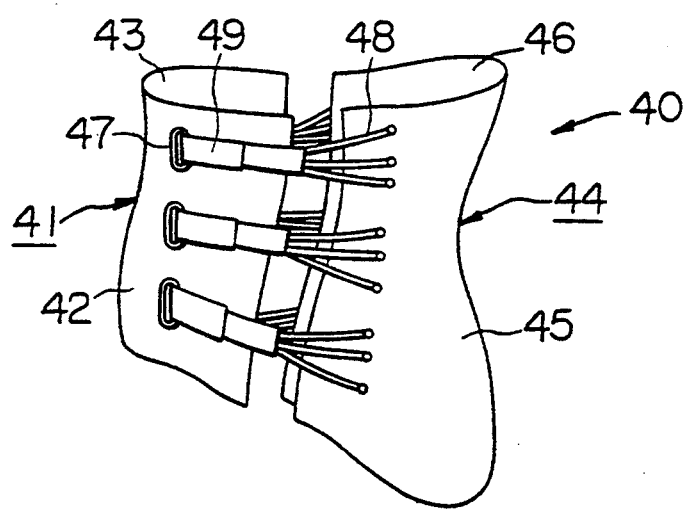
FIG. 7 is a side elevational view of a band used for lumbago treatment formed according to the teachings of the present invention.

FIG. 7 is a side elevational view of a band 40 which is used for lumbago treatment, the band 40 being formed with the sheet-like composition of the present invention. Reference numeral 41 identifies a front support plate with exterior composite fabric portion 42 and interior composite fabric portion 43, and reference numeral 44 identifies a back support plate with exterior composite fabric portion 45 and interior composite fabric portion 46. A plurality of squire rings 47, formed of metal, metal alloys, steels or plastic materials, are attached to both sides of front support plate 41 as a means of anchoring a plurality of fastening belts 49. A plurality of individual strings 48 or a single string of sufficient length, are secured on both sides of back support plate 44 opposite the location of squire rings 47 as shown in FIG. 7, the strings 48 being linked to fastening belts 49. As in the case of the cervical vertebra collar 30 illustrated in FIG. 6, band 40 is prepared by the following steps: apply, moisten and shape two sheet-like compositions, one composition to be applied to the abdomen and one composition to be applied to the back, these sheet-like compositions being molded to form the support plates 41 and 44, respectively; align the vertical edge end portions of the front and back support plates 41 and 44 and attach the squire rings 47, strings 48, and belts 49 so that the plates 41 and 44 can be fastened together on both sides as illustrated in FIG. 7.

The test results given below in Table 1 compare the properties of various embodiments of the composite fabric and foam material elements of the present invention with the properties associated with conventional materials. Samples of the test fabrics and materials were cut into rectangular shapes, each about 50 mm wide and about 200 mm long, and each were measured as follows:

Measurement 1: Weight in dry state: weigh the sample with a direct-reading balance and divide the weight by the sample size to convert the obtained weight into the normalized weight per area (g/m$^2$).

Measurement 2: Weight in wet state: dip the sample in a bath containing tap water; take the sample out of the water bath, lightly shake to remove water and weigh the sample; convert the weight into the weight per area (g/m$^2$) as calculated for the dry weight in Measurement 1.

Measurement 3: Amount of held water: calculate the difference between the weight in wet state (Measurement 2) and the weight in dry state (Measurement 1).

Measurement 4: Weight after short-time drying: place the wet sample from Measurement 2 for 5 minutes in a stream of warm air at 37° C. and then weigh the sample.

Measurement 5: Amount of residual water: calculate the difference between the weight after short-time drying (Measurement 4) and the weight in dry state (Measurement 1).

Measurement 6: Thickness: measure the thickness in dry state with a Peacock meter without applying load.

Measurement 7: Mesh: count the number of pores within a square inch area on the front face and on the back face.

The materials of the test samples of the present invention analyzed as indicated above and included in the below-referenced Table 1 are as follows:

Sample 1: Honeycomb-mesh triple-layered fabric whose front face and back face are made of 250d/48f polyester multifilament and whose connecting thread is made of 220d/1f nylon monofilament.

Sample 2: Tripled-layered fabric having honeycomb-mesh built on a flat substrate tissue based on the same textile constitution as above.

Sample 3: Honeycomb-mesh triple-layered fabric article having mesh size different from that of sample 1, based on the same textile constitution as above.

Sample 4: Honeycomb-mesh triple-layered fabric whose front face and back face are made of 70d/24f nylon multifilament and whose connecting thread is made of 30d/1f nylon monofilament.

Sample 5: Honeycomb-mesh triple-layered fabric different from that of sample 4 although based on the same constitution as above.

Sample 6: Honeycomb-mesh triple-layered fabric different from that of samples 4 and 5 although based on the same constitution.

Sample 7: Triple-layered fabric having honeycomb-mesh built on a flat substrate tissue whose front face and back face are made of 50d/48f polyester filament and whose connecting thread is made of 20d/1f polyester monofilament.

Sample 8: Triple-layered fabric whose front face and back face are made of a flat tissue based on the textile constitution similar to that of sample 1.

The materials of the test samples of comparable conventional materials analyzed as indicated above and included in the below-referenced Table 1 are as follows:

Sample 9: Closed-cell Neoprene rubber foam.
Sample 10: Closed-cell polyethylene rubber foam.
Sample 11: Polyester nonwoven bandage.
Sample 12: Felt.
Sample 13: Open-celled polyurethane foam.

TABLE 1

| Sample | Weight in dry state g/m² | Weight in wet state g/m² | Amount of held water g/m² | Weight after short-time drying g/m² | Amount of residual water g/m² | Thickness mm | Mesh pc/inch |
| --- | --- | --- | --- | --- | --- | --- | --- |
| 1 | 522 | 762 | 240 | 546 | 22 | 7.0 | 18 |
| 2 | 636 | 970 | 334 | 733 | 97 | 6.0 | 25 Front 315 Back |
| 3 | 618 | 876 | 358 | 653 | 35 | 5.0 | 45 |
| 4 | 244 | 782 | 538 | 366 | 122 | 3.0 | 48 |
| 5 | 259 | 716 | 457 | 355 | 96 | 3.0 | 52 |
| 6 | 288 | 834 | 546 | 395 | 107 | 3.0 | 91 |
| 7 | 189 | 529 | 340 | 298 | 109 | 3.2 | 85 Front 135 Back |
| 8 | 631 | 1097 | 488 | 736 | 109 | 8.0 | 135 |
| 9 | 1207 | 1299 | 92 | 1266 | 59 | 5.0 | — |
| 10 | 327 | 419 | 92 | 333 | 6 | 10.0 | — |
| 11 | 170 | 1995 | 1825 | 1620 | 1450 | 4.0 | — |
| 12 | 625 | 2414 | 1789 | 2320 | 1695 | 5.0 | — |
| 13 | 266 | 2844 | 2578 | 2172 | 1906 | 5.0 | — |

As is clear from Table 1, whereas the amount of held water of the triple-layered fabrics or closed-cell foam materials of the present invention is not more than 600 g/m², the amount of held water of the conventional articles or materials is not less than 1500 g/m². As for the remaining water after drying for five minutes under an air stream at 37° C., the materials of the present invention retained an amount not more than 150 g/m² with almost no sense of residual moisture. Whereas the conventional articles or materials retained an amount not less than 1400 g/m², still retaining such an amount of water that, when pressed, water started to flow out. Such results explain why a drying period of one to two months is necessary before the conventional articles or materials become usable.

Figure 8A:
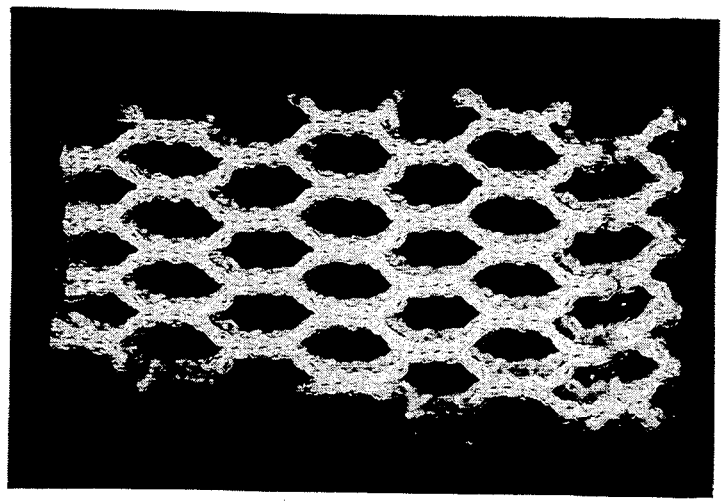
Figure 8B:
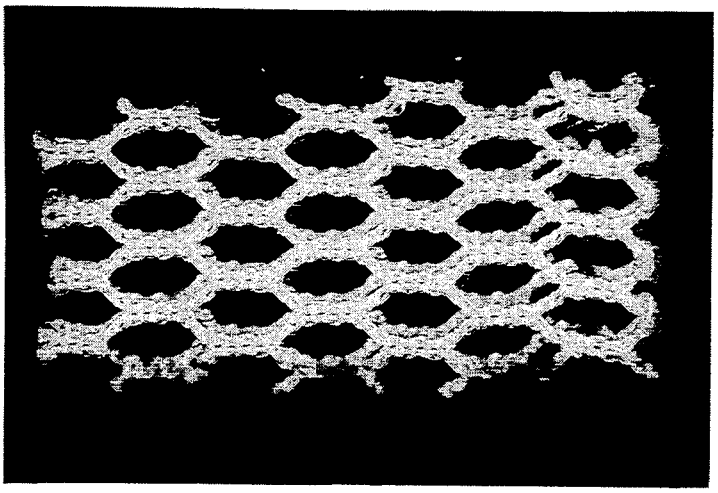
Figure 8C:
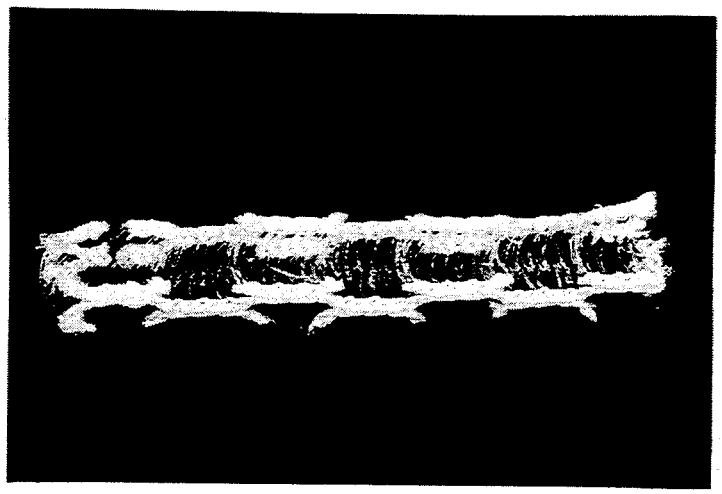

FIGS. 8a, 8b and 8c are photographs representing the textile shape of the honeycomb-mesh triple-layered fabric described as sample 1 above, where FIG. 8a is a view of the front or top face of the fabric FIG. 8b is a view of the back or bottom face of the fabric, and FIG. 8c is a side view showing the connecting thread portion.

Figure 9A:
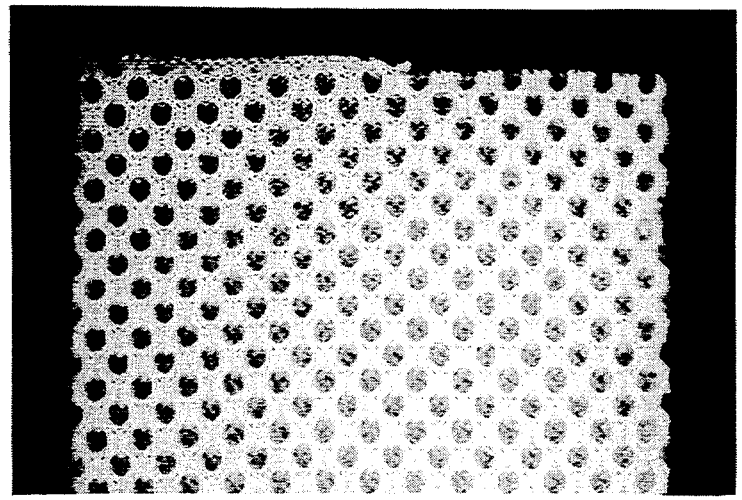
Figure 9B:
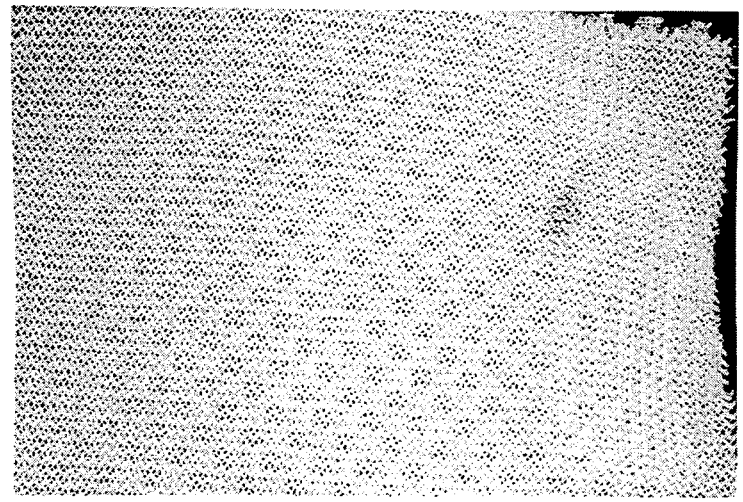
Figure 9C:
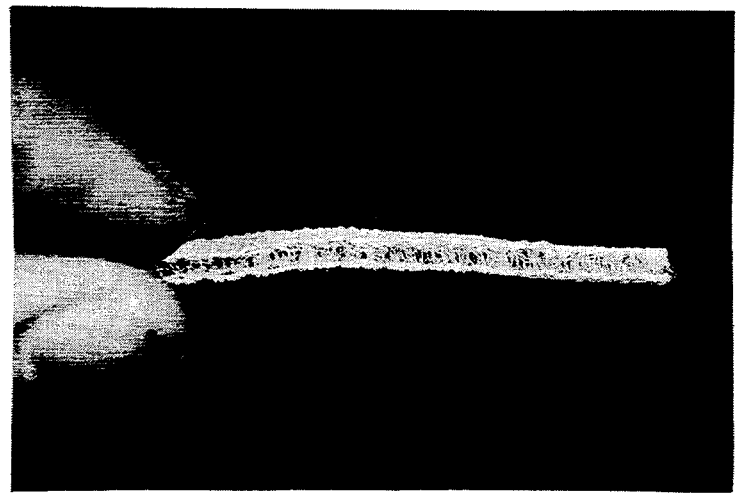

FIGS. 9a, 9b and 9c are photographs representing the textile shape of the triple-layered fabric described as sample 7 above, where FIG. 9a is a view of the front or top face of the fabric, FIG. 9b is a view of the back or bottom face of the fabric, and FIG. 9c is a side view showing the connecting thread portion.

Figure 10A:
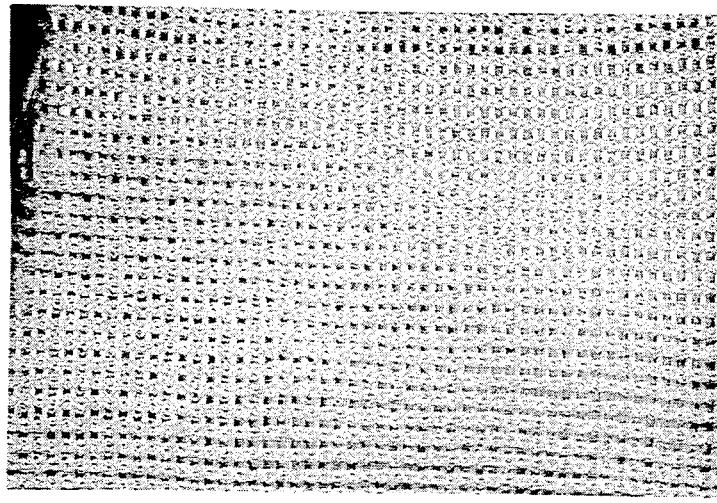
Figure 10B:
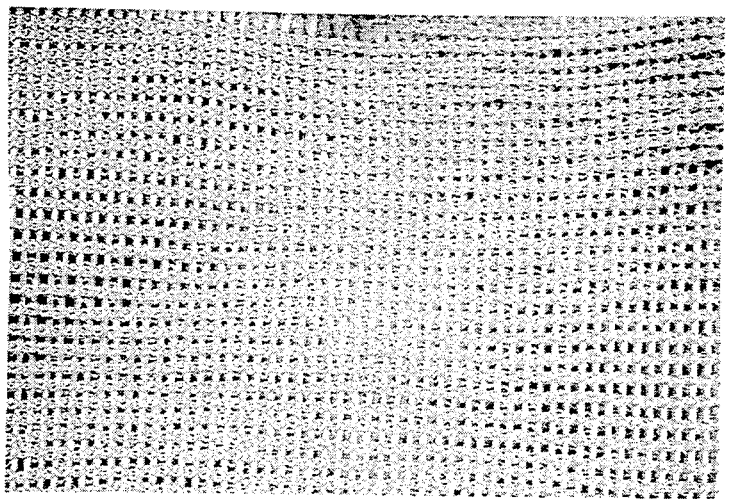
Figure 10C:
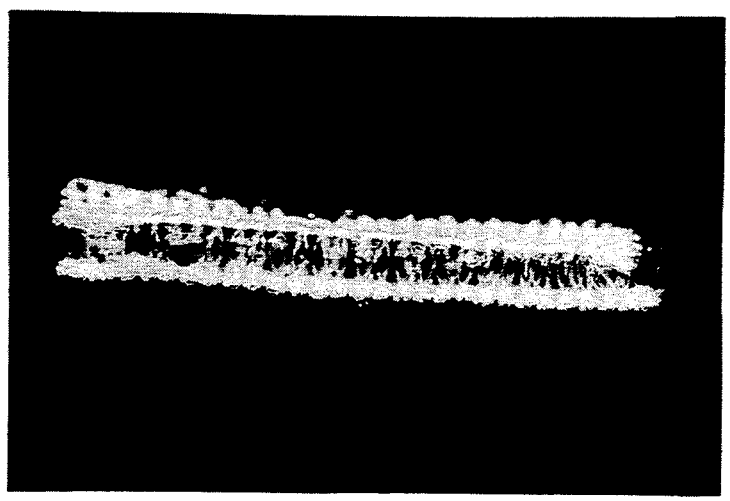

FIGS. 10a, 10b and 10c are photographs representing the textile shape of the triple-layered fabric described as sample 8 above, where FIG. 10a is a view of the front or top face of the fabric, FIG. 10b is a view of the back or bottom face of the fabric, and FIG. 10c is a side view showing the connecting thread portion.

Since the composition of the present invention is made by covering a pliant sheet impregnated with water-curable resin with a composite fabric having large voids between the fiber connecting the opposite faces of the fabric, water introduced to the outer surfaces of the composition easily infiltrates to the internal pliant sheet portion of the composition. Thus, when the sheet-like composition is brought into contact with water, an amount of water sufficient to initiate and complete the curing process contacts the inner pliant sheet. Furthermore, when the composition of the present invention is removed from the water contact and is lightly shaken, the excess water, which is more than that needed for the curing process, can almost all be removed. Remaining water further diffuses from the interstitial space of the connecting portion of the triple-layered fabric, thereby allowing articles formed of the present sheet-like composition to dry within a short period of time. Additionally, the heat generated when the water-curable resin cures and hardens is discharged through the interstitial space of the connecting part of the composite fabric portions so efficiently that the heat is not retained or transmitted to the body part and therefore prevents the wearer from suffering burns or other discomforts. Wearing devices formed of the composition of the present invention on the body, such as those shown in FIGS. 4-7, moreover does not cause such problems as accumulation of heat, stuffiness, unpleasant odor and growth of various bacteria, even when the temperature or humidity is high, because the triple-layered fabric portions assure improved air permeability. In addition, the interior sheet impregnated with a water-curable resin, after curing and hardening, does not directly contact or touch the body and, particularly, it does not touch the affected body part owing to the cushioning action of the compressible fibers forming the connecting portion of the composite fabric. The individual fabric portions of the sheet-like composition can deform in a multi-directional manner and thus prevents the formation of wrinkles in the hardened device, even if the present composition is used to form a device which conforms to a complex shape of a body part or a portion thereof. The surfaces of the composition as well as the finished device are kept relatively smooth and deformation-free to prevent any partial oppression or tension on the wearer. As a result, the composition of the present invention provides fitted devices having excellent overall wearing comfort, operationality and high therapeutic effect.

Thus there has been shown and described several embodiments of a novel sheet-like composition adaptable for use in forming a wide variety of orthopedic devices, which sheet-like compositions fulfill all the objects and advantages set forth above. Many changes, modifications, variations and other uses and applications of the present invention will, however, become apparent to those skilled in the art after considering this specification and the accompanying drawings. All such changes, modifications, variations and other uses and applications which do not depart from the spirit and scope of the invention are deemed to be covered by the invention which is limited only by the claims which follow.

What is claimed is:

1. An orthopedic sheet comprising a pliant sheet of material having opposed side surfaces, said pliant sheet being impregnated with a viscous water-curable resin that cures when exposed to water a first triple-layered fabric structure overlaying one side surface of said pliant sheet, and a second triple-layered fabric structure overlaying the other side surface of said pliant sheet, each of said first and second triple-layered fabric structures having a front face, a back face and an intermediate portion interconnecting said front and back faces.

2. The orthopedic sheet of claim 1 wherein the front face, back face and interconnecting portion of said first and second fabric structures are each made of natural fibers.

3. The orthopedic sheet of claim 1 wherein the front face, back face and interconnecting portion of said first and second fabric structures are each made of man-made fibers.

4. The orthopedic sheet of claim 3 wherein said man-made fibers are selected from the group consisting of inorganic fibers, regenerated man-made fibers, semi-synthetic fibers and synthetic fibers.

5. The orthopedic sheet of claim 1 wherein the front face, back face and interconnecting portion of said first and second fabric structures are each made of a combination of man-made fibers and natural fibers.

6. The orthopedic sheet comprising a pliant sheet having opposed side surfaces, said plaint sheet being impregnated with a viscous water-curable resin that cures when exposed to water, a triple-layered fabric material overlaying one side surface of said pliant sheet, a triple-layered fabric material overlaying the other side surface of said pliant sheet, and a closed-cell foam material interposed between one side surface of said pliant sheet and one of said triple-layered fabric materials, each of said triple-layered fabric materials having a front face, a back face and an intermediate portion interconnecting said front and back faces.

7. The orthopedic sheet of claim 6 wherein the front face, back face and interconnecting portion of said fabric materials are each made of natural fibers.

8. The orthopedic sheet of claim 6 wherein the front face, back face and interconnecting portion of said fabric materials are each made of man-made fibers.

9. The orthopedic sheet of claim 8 wherein said man-made fibers are selected from the group consisting of inorganic fibers, regenerated man-made fibers, semi-synthetic fibers and synthetic fibers.

10. The orthopedic sheet of claim 6 wherein the front face, back face and interconnecting portion of said fabric materials are each made of a combination of man-made fibers and natural fibers.

11. The orthopedic sheet of claim 6 wherein adhesive means are interposed between one of said fabric materials and one side surface of said pliant sheet, and adhesive means are interposed between said closed-cell foam material and the other of said fabric material.

* * * * *